United States Patent
Cardot et al.

[11] Patent Number: 6,124,631
[45] Date of Patent: Sep. 26, 2000

[54] MICRO SENSOR AND METHOD FOR MAKING SAME

[75] Inventors: Francis Cardot, Neuchâtel, Switzerland; Philippe Arquint, Herzogenaurach, Germany; Bart van der Schoot, Neuchâtel, Switzerland

[73] Assignee: Centre Suisse d'Electronique et de Microtechnique SA, Neuchatel, Switzerland

[21] Appl. No.: 08/842,875

[22] Filed: Apr. 17, 1997

[30] Foreign Application Priority Data

Apr. 26, 1996 [FR] France ................................. 96 05319

[51] Int. Cl.⁷ .......................... H01L 23/02; H01L 29/04; H01L 23/48; B32B 9/00
[52] U.S. Cl. .......................... 257/667; 257/687; 257/728; 257/724; 257/721; 257/714; 257/738; 257/777
[58] Field of Search .................................... 257/700, 786, 257/738, 737, 734, 777–779, 782, 687, 667, 712, 714, 721, 726, 727, 728, 783

[56] References Cited

U.S. PATENT DOCUMENTS

| | | | |
|---|---|---|---|
| 4,509,096 | 4/1985 | Baldwin et al. | 361/386 |
| 4,893,174 | 1/1990 | Yamada et al. | 257/621 |
| 5,084,752 | 1/1992 | Satoh et al. | 257/786 |
| 5,148,266 | 9/1992 | Khandros et al. | 257/773 |
| 5,187,020 | 2/1993 | Kwon et al. | 428/601 |
| 5,202,754 | 4/1993 | Bertin et al. | 257/684 |
| 5,279,711 | 1/1994 | Frankeny et al. | 174/263 |
| 5,504,035 | 4/1996 | Rostoker et al. | 438/106 |
| 5,517,344 | 5/1996 | Hu et al. | 359/8 |
| 5,523,628 | 6/1996 | Williams et al. | 257/777 |
| 5,659,203 | 8/1997 | Cell et al. | 257/778 |
| 5,681,647 | 10/1997 | Caillat | 428/209 |
| 5,753,972 | 5/1998 | Wein et al. | 257/691 |
| 5,767,580 | 6/1998 | Rostoker | 257/737 |
| 5,796,165 | 8/1998 | Yoshikawa et al. | 257/728 |
| 5,804,882 | 9/1998 | Tsukagoshi et al. | 257/783 |
| 5,818,113 | 10/1998 | Iseki et al. | 257/778 |
| 5,825,092 | 10/1998 | Delgado et al. | 257/778 |
| 5,834,835 | 11/1998 | Maekawa | 257/680 |
| 5,914,535 | 6/1999 | Brandenburg | 257/777 |

FOREIGN PATENT DOCUMENTS

| | | |
|---|---|---|
| 0 528 251 | 2/1993 | European Pat. Off. . |
| 0 695 941 | 2/1996 | European Pat. Off. . |

*Primary Examiner*—Alexander O. Williams
*Attorney, Agent, or Firm*—Griffin & Szipl, P.C.

[57] ABSTRACT

The invention concerns a device comprising a first substrate and a second substrate intended to form a micro-system such as a sensor, at least one of the substrates being able to include electronic circuit components. The invention is characterised in that a layer of polymer is interposed between the first and the second substrate, in that the polymer layer includes at least one cavity which extends from the first to the second substrate and in that solder attaching means are provided in the cavity, said solder means assuring a traction resistant mechanical connection between the two substrates.

6 Claims, 3 Drawing Sheets

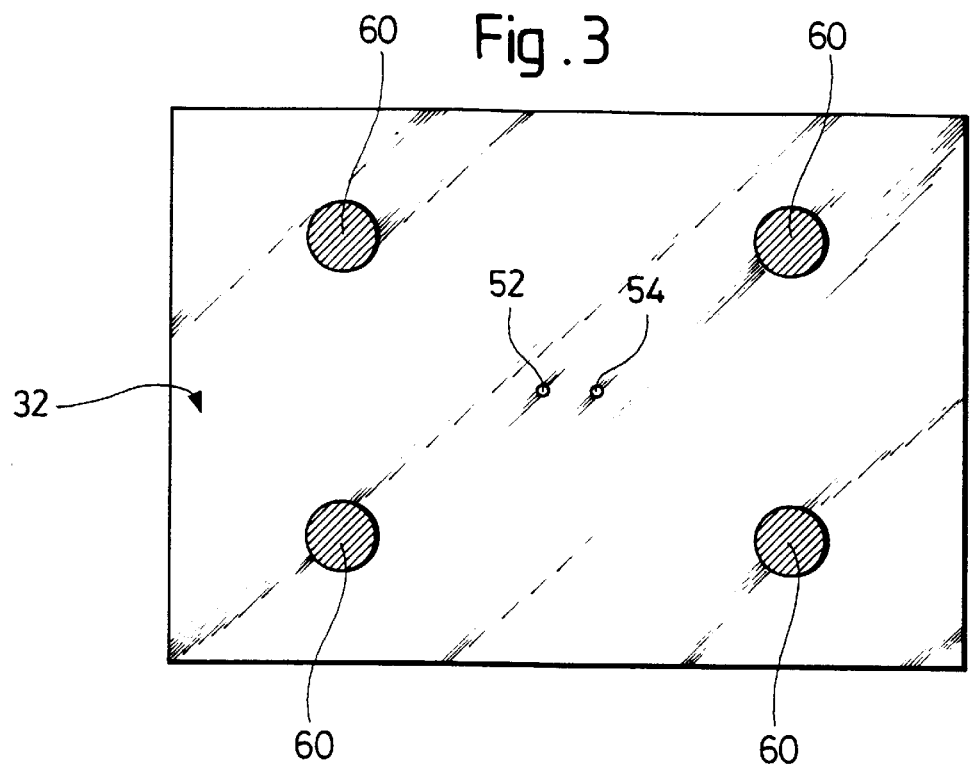
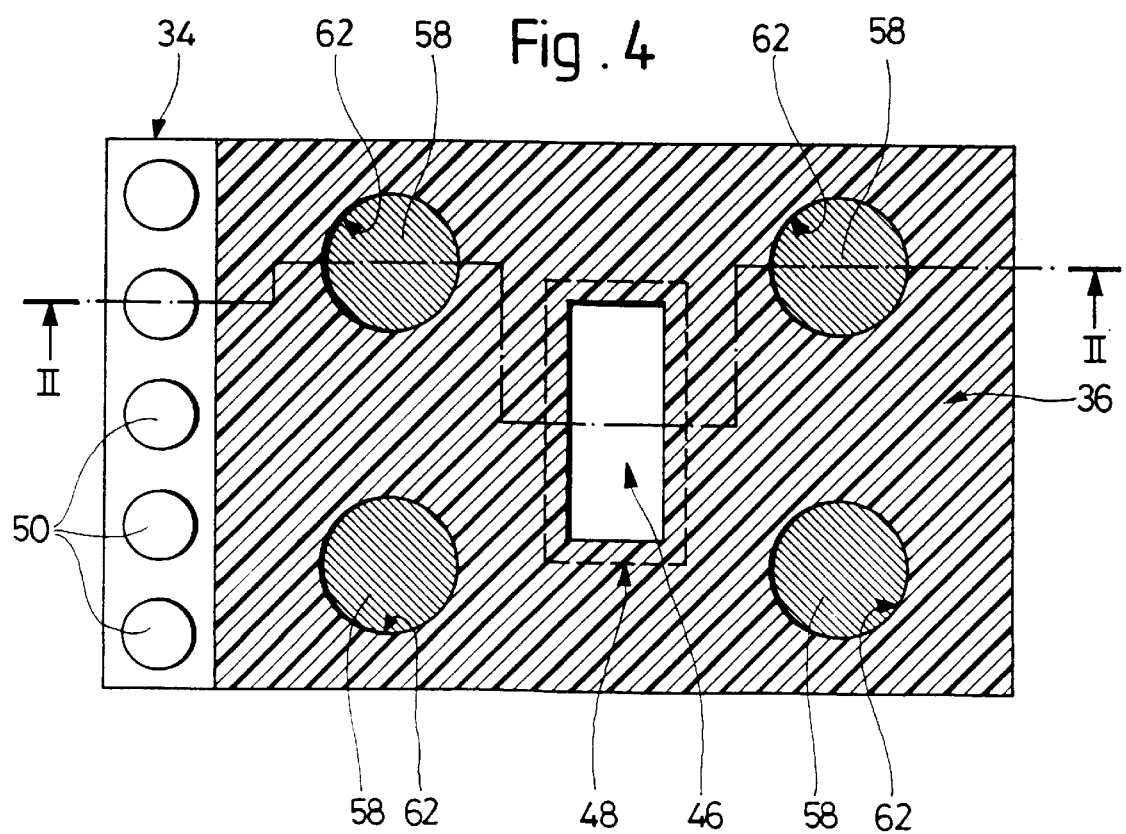

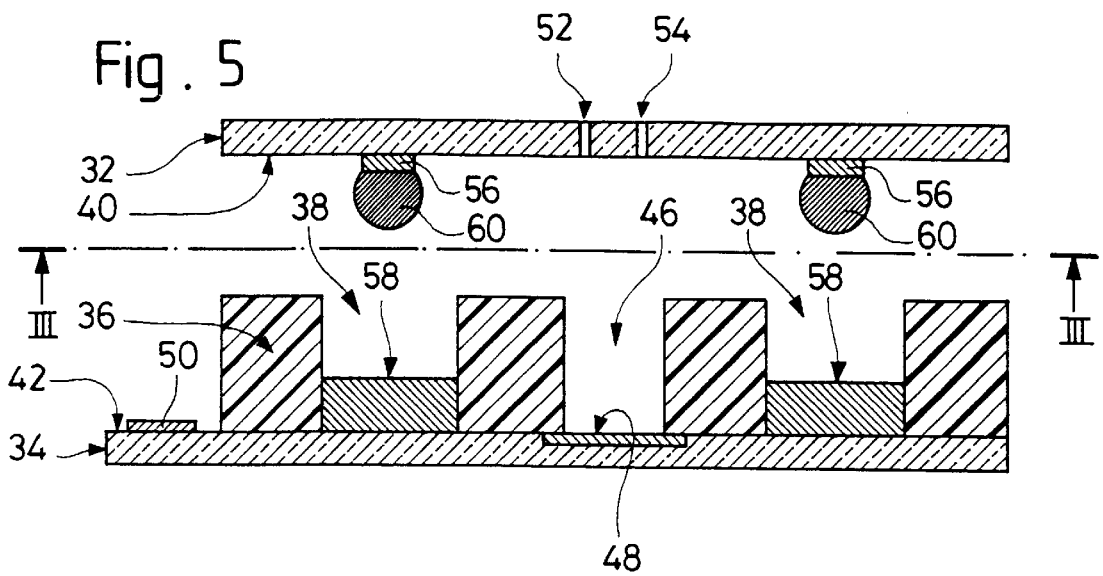
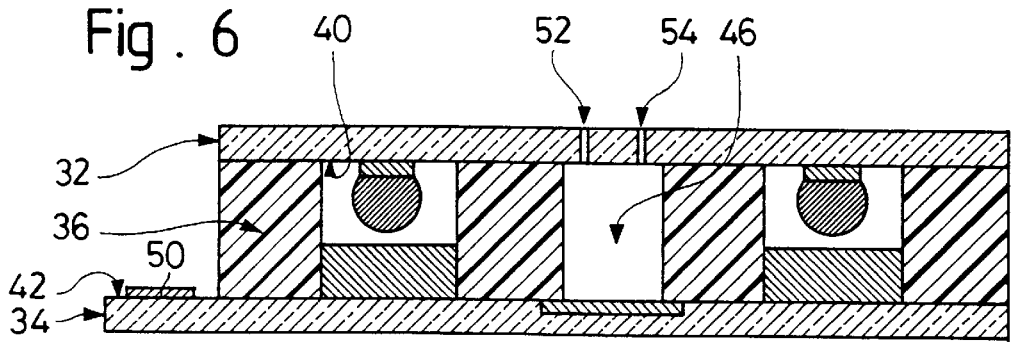
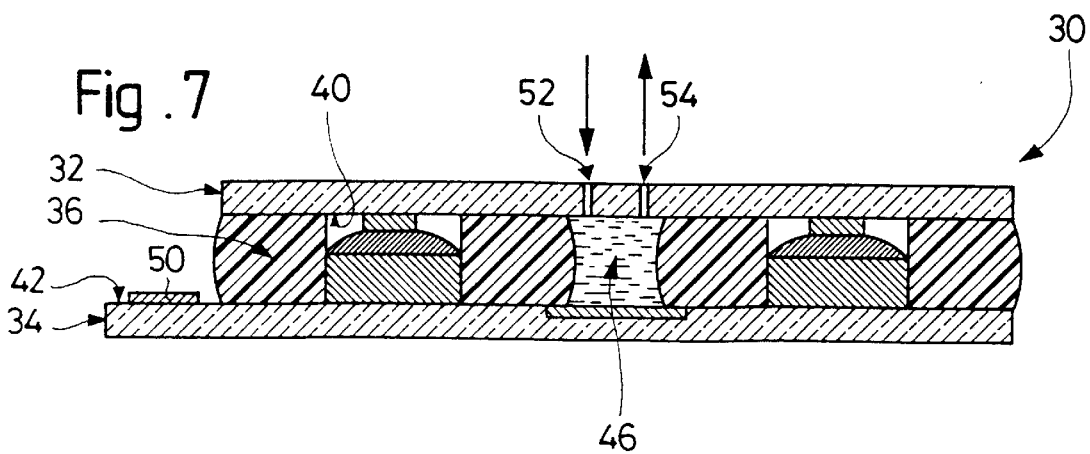

MICRO SENSOR AND METHOD FOR MAKING SAME

The invention generally concerns micro-machined devices, and more particularly, a device comprising at least two substrates intended to form a micro-system or par of a micro-system such as a sensor obtained for example by assembling at least two micro-machined substrates. The invention also concerns a method for assembling two micro-machined substrates, in particular for obtaining a device of the type mentioned above.

Devices comprising several substrates, for example a flow collector fitted with a chemical sensor such as a pH sensor, shown schematically in cross-section in FIG. 1, are already known.

A collector of this type comprises a first substrate 1 on one face 2 of which is fixed a sensor module 4 comprising for example a silicon plate in which is integrated a detection cell 6 comprising in particular measuring electrodes (not shown) which are respectively connected to corresponding contact pads 8. The contact pads are connected to contact bumps 10 attached to first substrate 1 by wire bonding 12, so as to establish a connection with an external measuring circuit (not shown).

The collector further comprises a second substrate 14 superposed onto first substrate 1, an O-ring seal 16 being interposed between the two substrates 1 and 14 so that the contour of seal 16 surrounds the zone of plate 4 including detection cell 6. Plate 4, O-ring seal 16 and substrate 14 thus delimit a sealed collecting chamber 18 within which a fluid may flow via an entry channel 20 and an exit channel 22 which are arranged in substrate 14 in a suitable manner. The sealing of chamber 18 as regards other elements of the device is achieved by holding the two substrates 1 and 14 tightly against each other by means of a screw gripping bracket system 24 or similar.

The use of such a gripping system has the drawback of being heavy and costly and of being difficult to implement.

Moreover, the use of an O-ring seal has the drawback of making it difficult to achieve perfect sealing in cases where the surfaces of the device in contact with the seal are not smooth but more or less highly structured, which is the case of numerous detection sensors.

The application of a seal of this type onto structured surfaces leads to risks of substantial leaks of the liquid to be tested in the device, which may damage surrounding elements, in particular in the event that the liquid to be tested contains aggressive reagents, or conversely may lead to risks of polluting the liquid flowing in the collecting chamber.

Thus, a principal aim of the invention is to overcome the drawbacks of the aforementioned prior art by providing a device comprising at least two substrates, intended to form a micro-system or part of a micro-system, which is easy and economical to implement and which, in the case of a device intended to carry a fluid, allows the elements of the device to be protected efficiently from the carried fluid by assuring the desired sealing.

The invention therefore concerns a device comprising a first substrate and a second substrate intended to form a micro-system, at least one of the substrates being able to comprise electronic circuit elements, characterised in that a layer of polymer is interposed between the first and second substrate, in that the layer of polymer comprises at least one cavity which extends from the first to the second substrate and in that solder attaching means are provided in the cavity, said attaching means assuring a traction resistant mechanical connection between the two substrates.

Screw gripping systems may thus be omitted for assembling the substrates, and a mechanical assembly by reliable soldering may be obtained. The O-ring seals used in the prior art are replaced by the layer of polymer which may, for example, be easily deposited on one of the substrates before they are assembled, this layer then marrying all the bulges exhibited by the substrate and thereby removing the aforecited sealing problems. It will be noted in this regard that a compressible polymer will preferably be selected for reasons which will become clearer during the description which follows.

According to an advantageous feature of the invention, the solder attaching means comprise bonding pads arranged respectively on each substrate and solder material connecting the bonding pad of the first substrate to the bonding pad of the second substrate.

This mechanical assembly may thus also assure in an advantageous manner an electric and thermal connection between the substrates, in order respectively, as required, to transfer an electric contact of one substrate onto the other and to contribute to a more efficient dissipation of the heat generated when the device is operating.

According to another feature of the invention, the polymer layer is compressed between the first and second substrate, and the solder material is subjected to a permanent traction force, the polymer being compressed between the two substrates.

The compression of the polymer layer between the two substrates thus allows one to assure a high level of sealing of the cavities in which the solder attaching means extend, as regards the exterior.

According to a preferred embodiment of the invention, the layer of polymer comprises a chamber intended to receive a fluid or a gas, arranged in the polymer layer, the polymer of the layer assuring the sealing between the chamber and the cavity and/or the exterior.

In this manner, advantage is taken of the polymer layer to form also therein functional means of the device, in particular sealed cavities or collecting chambers of any shape in which a fluid to be tested may flow, the solder attaching means being protected and insulated from the cavities in which a fluid or gas flows by the polymer layer, so that the fluids to be tested are also protected if necessary against any pollution by the metals used for soldering.

According to a preferred feature of the invention, the polymer of the layer is a polymer belonging to the polysiloxane family.

Such polymers have the advantage of being able to undergo double polymerisation and thus of being able to adhere to the substrates during the second polymerisation, thereby increasing the sealing and the cohesion of the device.

According to another aspect, the invention concerns a method for assembling two substrates, characterised in that it consists of providing a first substrate comprising on one of its faces at least a first bonding pad, providing a second substrate, depositing on one face of the second substrate a layer of photosensitive polymer, structuring the layer of photosensitive polymer to form at least one cavity opening out onto said face, providing in said cavity a second bonding pad intended to be connected to said first bonding pad, depositing solder material onto at least one of said first and second bonding pads, placing the face of the first substrate comprising the bonding pads onto the polymer layer so that the first bonding pad is situated facing the cavity, assembling the first and second substrates by soldering the first and second bonding pads.

It will be noted that according to this method, advantage is taken of the structuring of the polymer layer to use the cavity or cavities as a mould for forming the bonding pads, for example for the galvanic growth of a metal intended to form the bonding pad.

Moreover, the use of this polymer layer allows sealing means having any form and width to be achieved as a function of the desired application.

Other features and advantages of the invention will appear more clearly upon reading the following description of an embodiment of the invention given purely by way of illustrative and non-limiting example, this description being made in conjunction with the drawings in which:

FIGS. 3 and 4 are elevation views respectively of the upper and lower substrates of the micro-system of FIG. 2 prior to assembly; and FIGS. 5 to 7 are cross-section of the device of FIG. 2 shown during different steps of the method for assembling two substrates according to the invention.

Figure 1:
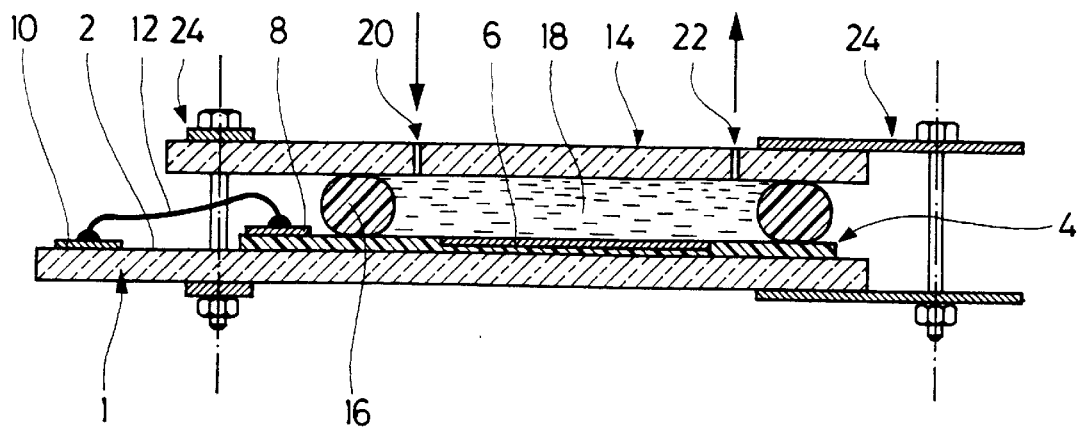
FIG. 1 is a cross-section of a device of the prior art.
Figure 2:
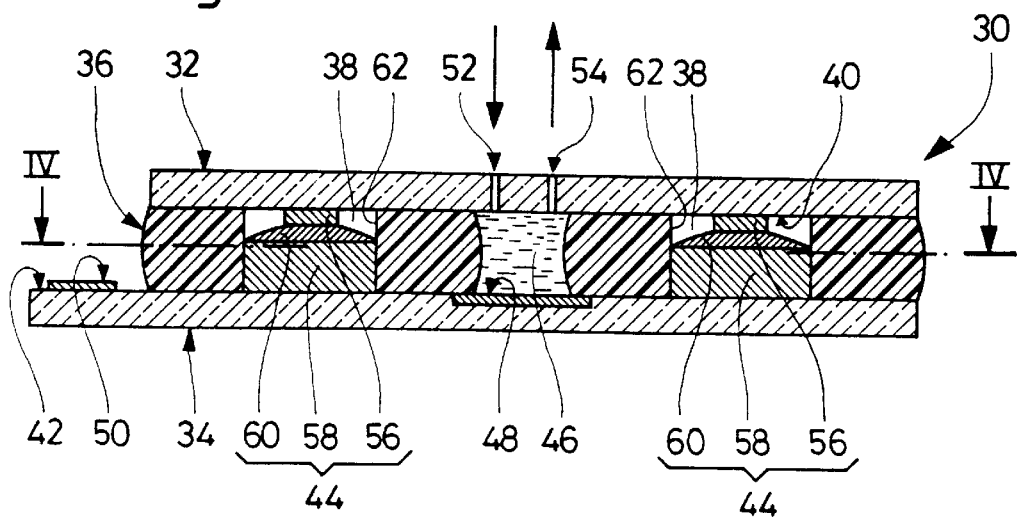
FIG. 2 is a cross-section of a micro-system comprising two substrates assembled according to the invention.

Referring to FIGS. 2 to 4, a cross-section of an embodiment example of a device intended to form a micro-system is shown, in this case a part of a chemical sensor such as a pH sensor, designated by the general numerical reference 30.

It will be noted first that the drawing does not show the exact relative dimensions of the elements in relation to each other and that the dimensions have been greatly exaggerated for greater clarity. By way of indication, the general dimensions of a device of this type are in the order of 10×10×1 $mm^3$.

Device 30 comprises a first substrate 32 and a second substrate 34 between which a compressible polymer layer 36 is interposed. By way of example, the substrates may be made of a semi-conductive material such as silicon.

Polymer layer 36 is preferably made from a polymer having photosensitive properties for reasons which will appear hereinafter and which preferably belongs to the polysiloxane family.

Polymer layer 36 comprises four cavities 38 extending between two opposite faces 40 and 42 of substrates 32 and 34, solder means 44 assuring the mechanical connection between substrates 32 and 34 being provided in such cavities.

In the application illustrated in the drawings, polymer layer 36 comprises a collecting chamber 46 intended to receive a sample of liquid or gas to be tested and in which is provided a detection cell 48, which, in the example illustrated, is a pH detection cell. Detection cell 48 has for example a plurality of integrated electrodes in substrate 34 which are connected to contact pads 50 situated outside chamber 46.

This collecting chamber 46 is fed via an entry channel 52 which is provided in substrate 32. After coming into contact with detection cell 48, the liquid or gas is evacuated from chamber 46 via exit channel 54.

Solder means 44 comprise bonding pads 56, 58, respectively arranged on faces 40, 42 of substrates 32 and 34 in cavities 38, and soldering material 60 which connects bonding pads 56 of substrate 32 to bonding pads 58 of substrate 34. The bonding pads are made of metal and preferably these bonding pads are made of nickel. Of course, any other metal suitable for forming a mechanical connection between the substrate and the solder material may be used.

Bonding pads 56, 58 of substrates 32 and 34 are connected by means of solder material 60, preferably a lead and tin alloy solder.

In order to assure good sealing of collecting chamber 46 as regards the exterior of the device on the one hand and cavities 38 as regards the exterior of the device on the other hand, polymer layer 36 is compressed between substrates 32 and 34 so that the solder connection 44 is subjected to a traction force exerted by the compressed polymer.

Polymer layer 36 is preferably attached to at least one of substrates 32, 34. In this regard, one will choose to form the polymer layer on the substrate whose surface in contact with said polymer layer comprises the greatest structuration or the most significant bulges. However, as will be seen hereinafter in connection with the description of the assembly method, at the moment of soldering, the assembly of the two substrates with the polymer layer is compressed and undergoes a rise in temperature to reach the fusion temperature of the solder material, which allows a second polymerisation of the polymer to be achieved during which connection of the polymer layer with the substrates is created.

Of course, polymer layer 36 may, according to an alternative embodiment, be made in the form of a sheet which is not attached to either of the substrates and be prepared separately with a suitable structuration of the cavities. In such case, the structured sheet is simply held compressed between the substrates by the solder connection.

Referring henceforth to FIGS. 5 to 7, the method for assembling two substrates, in particular for obtaining the device or micro-system 30 which has just been described, will be described. In FIGS. 5 to 7, the same elements as those described in connection with FIGS. 2 to 4 bear the same numerical references.

Although the method of the invention allows the assembly of two substrates for simultaneously obtaining a plurality of functional micro-systems, the description and the figures will, for the sake of simplicity, relate only to a single functional device. The method is preferably a batch method which allows a plurality of devices to be simultaneously manufactured on a same wafer.

The wafers forming first and second substrates 32 and 34 from which device or micro-system 30 is manufactured, are preferably made of a semi-conductive material such as silicon.

FIG. 5 shows first substrate 32 after the formation on face 40 of bonding pads 56 and the deposition on such bonding pads of solder material 60, and second substrate 34 after the formation of layer 36 and bonding pads 58.

The formation of bonding pads 56 is achieved in a conventional manner by vacuum evaporation of a metal, for example nickel or aluminium, through a mask (not shown). Of course, such bonding pads 56 and 58 may also be made by any other means, for example via cathode sputtering. Solder material 60 is also deposited in the same manner on pads 56 through a mask.

In order to make 34 as it is shown in FIG. 5, a layer of photosensitive material 36 has been deposited on its face 42, for example by centrifugation. The upper surface thereby obtained is flat and smooth which improves the sealing when it is applied against the other substrate. Furthermore, the polymer layer marries any bulges, which the face of the substrate on which it is deposited, might comprise. Then, polymer layer 36 has been exposed to light through a mask (not shown) having a suitable shape. The exposed parts of polymer layer 36 have then be removed in a conventional manner, for example by wet means, in order to form cavities 38 and collecting chamber 46 until surface 42 of substrate 34 appears.

The polymer forming layer 36 will preferably be a polysiloxane, this photosensitive polymer having good planarisation properties and being able to undergo double polymerisation thereby also giving it additional adhesion properties. Moreover, this polymer is able to compress well.

The following step consists of forming bonding pads 58 on the bottom of cavities 38 which have just been formed in layer 34. In order to do this, cavities 38 are preferably used as moulds for galvanically growing a metal intended to form bonding pads 58. The metal used to form these bonding pads 58 is preferably nickel.

It is obvious to the man skilled in the art that the galvanic growth operation requires, previously, the formation of electrodes on the bottom of cavities 38. Such formation of electrodes could be achieved by any suitable known means.

During the following step, shown in FIG. 6, substrates 32 and 34 are placed on top of each other so that bonding pads 56 provided with solder material 60 respectively penetrate corresponding cavities 28 arranged in polymer layer 36 and thus are facing corresponding bonding pads 58.

Once the two substrates 32 and 34 are thus prepared, they are put in place in a solder-aligner device (not shown) in which sufficient pressure is applied to them to compress layer 34 while being heated to a sufficient temperature to cause soldering material 60 to melt, and to achieve the solder connection of bonding pads 56 and 58. In the case of use of a lead/tin alloy as solder material, the assembly of the two substrates will typically be heated so that the solder material reaches a temperature of around 200° C.

It will be noted that during the galvanic growth operation, care will be taken that the thickness of bonding pads 58 is sufficient so that when substrates 32 and 34 are superposed and the polymer layer is compressed, the solder material comes into contact with the bonding pads which it has to connect.

According to the application, the bonding pads connected to integrated electronic components of the substrate and the solder means also assure transfer of an electric contact from one substrate to another.

The device which has just been described finds application in particular in the field of fluidics, chemical or biological sensors, ink jet printing heads and suchlike.

What is claimed is:

1. A device comprising a first substrate and a second substrate forming a sensor, at least one of the substrates including an electronic circuit element, wherein a layer of polymer is interposed between the first and the second substrate, wherein the polymer layer includes at least one cavity (28) which extends from the first to the second substrate, and wherein solder attaching means assuring a traction resistant mechanical connection between the two substrates are provided in the cavity (28), and wherein said device further comprises a collecting chamber (46) for receiving a sample consisting essentially of a member selected from the group consisting of a fluid and a gas, arranged in the polymer layer, the polymer of the layer assuring the sealing between the chamber (46) and the cavity (28) and the exterior.

2. A device according to claim 1, wherein the solder attaching means comprise bonding pads arranged respectively on each substrate and solder material connecting the bonding pad of the first substrate to the bonding pad of the second substrate.

3. A device according to claim 1, wherein the polymer layer is compressed between the first and the second substrate, and wherein the solder is subjected to a permanent traction force, the polymer being compressed between the substrates.

4. A device according to claim 1, wherein the polymer belongs to the polysiloxane family.

5. A device according to claim 1, wherein the bonding pads are metal pads, preferably made of nickel, and in that the solder is a lead/tin alloy solder.

6. A device according to claim 1, wherein a detection cell (48) is provided In said collecting chamber.

* * * * *